United States Patent [19]

Cottrell et al.

[11] Patent Number: 5,308,978

[45] Date of Patent: May 3, 1994

[54] METHOD OF PREPARING A SAMPLE FOR ANALYSIS

[75] Inventors: John S. Cottrell, London, United Kingdom; Kuldip K. Mock, Sunnyvale, Calif.

[73] Assignee: Finnigan Mat Limited, United Kingdom

[21] Appl. No.: 835,969

[22] PCT Filed: Jun. 25, 1990

[86] PCT No.: PCT/GB90/00973

§ 371 Date: Feb. 20, 1992

§ 102(e) Date: Feb. 20, 1992

[87] PCT Pub. No.: WO91/03068

PCT Pub. Date: Mar. 7, 1991

[30] Foreign Application Priority Data

Aug. 23, 1989 [GB] United Kingdom ............... 8919191

[51] Int. Cl.$^5$ ............................................. H01J 49/04
[52] U.S. Cl. .................................. 250/288; 250/282
[58] Field of Search ................. 250/288, 288 A, 282, 250/281

[56] References Cited

U.S. PATENT DOCUMENTS

| | | | |
|---|---|---|---|
| 4,920,264 | 4/1990 | Becker | 250/288 |
| 4,988,879 | 1/1991 | Zare et al. | 250/288 |
| 5,045,694 | 9/1991 | Beavis et al. | 250/288 |
| 5,077,470 | 12/1991 | Cody et al. | 250/288 |
| 5,135,870 | 8/1992 | Williams et al. | 250/288 |
| 5,146,088 | 9/1992 | Kingham et al. | 250/288 |
| 5,188,937 | 6/1992 | Hillenkamp et al. | 250/288 |

FOREIGN PATENT DOCUMENTS 62-43562 2/1987 Japan.
62-284256 12/1987 Japan .................................. 250/288

OTHER PUBLICATIONS

Karas et al, "Matrix Assisted Ultraviolet Laser Desorption of Non-volatile Compounds", International Journal of Mass Spectrometry and Ion Processes, vol. 78 (1987), pp. 53–68.

Wright et al., "Matrix Enhanced Laser Desorption in Mass Spectrometry and Tandem Mass Spectrometry", Biomedical Mass Spectrometry, vol. 12 No. 4 (1985), pp. 159–162.

Davis et al., "Identification of Naturally Occuring Quaternary Compounds by Combined Laser Desorption and Mass Spectrometry", Analytical Chemistry, vol. 55 No. 8 (Jul 1983), pp. 1302–1305.

Shomo et al., "Laser Desorption Fourier Transform Ion Cyclotron Resonance Mass Spectrometry vs Fast Atom Bombardment Magnetic Sector Mass Spectrometry for Drug Analysis", vol. 57 No. 14 (1985), pp. 2940–2944.

*Primary Examiner*—Paul M. Dzierzynski
*Assistant Examiner*—Kiet T. Nguyen
*Attorney, Agent, or Firm*—Flehr, Hohbach, Test, Albritton & Herbert

[57] ABSTRACT

A sample for analysis by Laser Desorption Mass Spectrometry is prepared by dissolving the sample material in a solvent and applying the solution to a matrix material. The matrix material is applied to a target for a mass spectrometer prior to the application of the sample solution thereto.

3 Claims, 1 Drawing Sheet

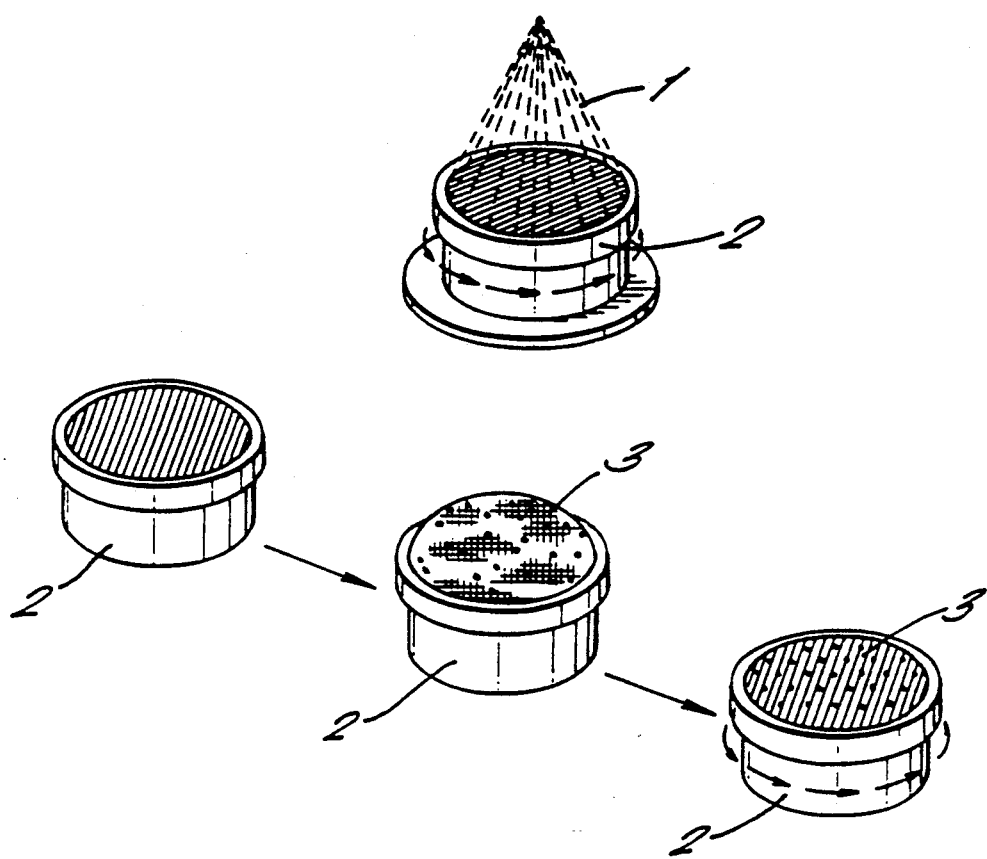
FIG.—1

METHOD OF PREPARING A SAMPLE FOR ANALYSIS

BACKGROUND OF THE INVENTION

This invention relates to a method of preparing a sample for analysis, and particularly a sample for analysis by Laser Desorption Mass Spectrometry (LDMS) in which ions are sputtered from a condensed phase sample surface by photon bombardment and are then subjected to mass analysis.

Many methods of LDMS are known, and a feature common to many is the use of a matrix material in which the analyte (the sample material to be analysed) is dispersed. The matrix material can serve one or more of a plurality of functions. For example it may act as a mediator in transferring energy from the photon bombardment to the sample material molecules; it may provide a physical and chemical environment which enhances the probability of desorption in the desired state of charge and aggregation; it may remove excess energy from the desorbed species through evaporation of matrix material molecules from a desorbed cluster of sample material and matrix material ions; and it may assist in the isolation and purification of the sample material.

Four techniques for using a matrix material to enhance LDMS have been described as set out below.

The first is to dissolve the sample material together with a 10:1 excess of an inorganic salt in a solvent, place a drop of the solution on the target surface, and evaporate to dryness as described by D. V. Davis et. al. in Analytical Chemistry, 55 1302 (1983). The sample material deposit is then irradiated with infra-red photons from a pulsed Neodymium YAG laser.

The second is to mix equimolar amounts of sample material and an inorganic salt in a droplet of glycerol placed on the target surface as described by L. G. Wright et. al. in Biomedical Mass Spectrometry, 12 159 (1985). The sample mixture is then irradiated with infrared photons from a continuous wave carbon dioxide laser.

Thirdly, Japanese Patent Specification JP62-43562 discloses a sample preparation technique in which a solution of the sample material is mixed with a slurry of glycerol and fine cobalt powder. A droplet of the mixture is then irradiated with ultraviolet photons from a pulsed nitrogen laser.

Fourthly, M. Karas et. al. (Int. J. Mass Spectrom. Ion Processes, 78 53 (1987)) describe using a large molar excess of a matrix material which has a strong absorption at the wavelength of the incident radiation. For example, the sample material is dissolved in a solution containing a thousand-fold molar excess of Nicotinic Acid. A drop of the solution is placed on the target surface, evaporated to dryness, and irradiated with 266 nm ultraviolet photons from a frequency quadrupled pulsed Neodymium YAG laser. The use of a matrix material which has a strong absorption for the incident photons represents an important distinction between this approach and the first three described because it allows the use of low power densities which increases the probability of desorbing intact molecular ions.

SUMMARY OF THE INVENTION

According to this invention there is provided a method of preparing a sample for analysis by laser desorption mass spectrometry, comprising dissolving the sample material in a solvent and applying the solution to a matrix material, in which the matrix material is applied to a target for a mass spectrometer prior to the application of the sample solution thereto.

The invention provides a method which is simple and economical to carry out, and is of particular use when the quantity of sample material available for analysis is very limited since it can be very difficult to mix a small amount of sample material solution and a small amount of a matrix material solution together on a target.

BRIEF DESCRIPTION OF THE DRAWINGS

The foregoing and other objects of this invention will be more clearly understood from the following description when read in conjunction with the accompanying drawings, wherein: FIG. 1 shows an embodiment of the present method for preparing a sample for analysis.

DETAILED DESCRIPTION OF THE INVENTION

Preferably the matrix material is at least partially soluble in the solvent in which the sample material is dissolved, since then some or all of the matrix material deposited on the target will dissolve in the applied sample material solution. This method is of particular advantage if the matrix material is applied to the target by a technique such as electrospraying which provides a matrix material deposit with a very large surface area. Otherwise the matrix material can be applied to the target by aerosol spraying, spin casting or evaporation.

However, it is not necessary to use a solvent in which both the sample and matrix materials have specific degrees of solubility.

Preferably the matrix material has a strong absorption for the photon bombardment used for mass spectrometry.

The invention will now be described by way of example with reference to the drawing which illustrates a method of sample preparation in accordance with the invention.

Referring to FIG. 1, a matrix material 1 which is partially soluble in the solvent in which the sample material for analysis, in this case a peptide, is dissolved, for example Nicotinic Acid, is electrosprayed in known manner onto the central region of a rotated target stage 2 of a mass spectrometer. A mask may be used to ensure that the matrix material 1 is restricted to a well defined area of known diameter. The electrospray technique is described fully by C. J. McNeal et. al. in Analytical Chemistry, 51 2036 (1979). A drop of sample material solution 3, for example a $10^{-5}$ molar solution of the peptide in 0.1% aqueous Trifluoroacetic Acid is placed onto the target 2 so as to cover the matrix material deposit and allowed to dry.

The loaded target 2 can then be introduced into the source region of a mass spectrometer for analysis of the sample material by bombardment with 266 nm photons from a frequency quadrupled Neodymium YAG laser, in known manner.

What is claimed is:

1. A method of preparing a sample for analysis by laser desorption mass spectrometry, comprising dissolving the sample material in a solvent and applying the solution to a matrix material, in which the matrix material is at least partially soluble in the solvent in which the sample material is dissolved, and in which the matrix material is applied to a target for a mass spectrometer prior to the application of the sample solution thereto.

2. A method as claimed in claim 1 in which the matrix material has a strong absorption for the photon bombardment used for mass spectrometry.

3. A method as claimed in claim 1 in which the matrix material is applied to the target by electrospraying.

* * * * *